United States Patent [19]

Gazzani

[11] Patent Number: 5,126,331
[45] Date of Patent: Jun. 30, 1992

[54] COMPOSITIONS FOR TOPICAL USE CONTAINING DEPOLYMERIZED DEOXYRIBONUCLEIC ACIDS IN THE SKIN AND BODY COSMETIC TREATMENT

[75] Inventor: Giovanni Gazzani, Como, Italy

[73] Assignee: Crinos Industria Farmacobiologica S.p.A., Como, Italy

[21] Appl. No.: 568,125

[22] Filed: Aug. 16, 1990

[30] Foreign Application Priority Data

Sep. 7, 1989 [IT] Italy .................. 21650 A/89

[51] Int. Cl.⁵ .................................. A61K 31/00
[52] U.S. Cl. ............................ 514/44; 536/27; 536/28; 536/29; 514/860; 514/886; 514/887
[58] Field of Search ............. 536/27, 28, 29; 424/70; 514/880, 44, 860, 886, 887

[56] References Cited

U.S. PATENT DOCUMENTS 4,046,879 9/1977 Swetly .................................. 514/44
4,557,934 12/1985 Cooper .................................. 514/165

Primary Examiner—Johnnie R. Brown
Assistant Examiner—J. Oliver Wilson
Attorney, Agent, or Firm—Nikaido, Marmelstein, Murray & Oram

[57] ABSTRACT

Compositions for topical use containing as active ingredients depolymerized deoxyribonucleic acids can be used for the reduction of the unaesthetisms of the face skin, due to the couperose. Said compositions can be advantageously used also to locally reduce, in the lower limbs, the skin unaesthetisms (dilated capillaries, oedemas, tumefactions), resulting from a situation of an extended physical stress acting on the above-mentioned legs.

5 Claims, No Drawings

COMPOSITIONS FOR TOPICAL USE CONTAINING DEPOLYMERIZED DEOXYRIBONUCLEIC ACIDS IN THE SKIN AND BODY COSMETIC TREATMENT

The present invention relates as first object to the use by topical way of formulations containing depolymerized deoxyribonucleic acids for the reduction of unaesthetisms of the face skin, due to couperose.

Another object of the invention relates to the topical use of said formulations to reduce unaesthetisms appearing in some skin areas of the lower limbs and which can be attributed to extended fatigue of the leg. For example, it may occur in subjects who during the working times are compelled to stand on their feet for extended periods of time.

In those cases, as a matter of fact, on the skin of the legs and of the ankles there may appear unusually dilated capillary vessels, combined with oedemas, tumefactions etc. In other skin areas the skin of the leg may, on the contrary, appear livid-coloured or pale.

Under those conditions, in the area of the leg involved by the afore-mentioned phenomena also a sensation of pain and/or heaviness can be felt.

The active ingredients of the subject formulations, namely the deoxyribonucleic acids with low molecular weight, are prepared through known depolymerizing processes. More particularly, said active ingredients are preferably obtained through the method of the U.S. Pat. No. 3,899,481.

The related chemical and chemico-physical properties of depolymerized deoxyribonucleic acids which are obtained according to this process are reported in Table I. The analytical methods which have been used for the determination of the related parameters have already been described in the European Patent Application No. 88-115,824, relating to the cosmetic use of the aforesaid substances as hair growth factors, to which reference is made.

Before describing the experiments by which the efficiency of the formulations containing depolymerized deoxyribonucleic acids in the uses foreseen by the present invention has been demonstrated, it seems proper to specify what is to be meant by the term "couperose", since in the literature of the field it has been variously used depending on the presence and importance in the skin of some characters by which it can be evidenced.

In the Dermatology Books this skin pathology is more properly defined as teleangiectasic erythrosis, since couperose causes the more or less extended reddening of the face skin, in which dilated surface blood vessels are detectable (teleangiectasis).

It is to be noted that the above-mentioned reddening can be extended to the whole face, or it can be localized in determined areas, such as for example on the cheekbones, on the nose or under the eyes.

The teleangiectasies which have been above-mentioned and accompany, as seen, the face reddening, sometimes may assume characteristical forms which are named, depending on the cases, "star-like", "band-like", "hair-like".

TABLE I

| Chemical and chemico-physical analytical parameters of the depolymerized deoxyribonucleic acids which can be used for the purposes foreseen by the present invention. | | |
| --- | --- | --- |
| Phosphorus | (+) | 8.0–9.6 |
| Nitrogen | (+) | 13.0–15.0 |
| Deoxyribose | (+) | 17.0–24.0 |
| Adenine | (+) | 8.0–11.0 |
| Guanine | (+) | 7.0–9.5 |
| Cytosine | (+) | 5.5–7.5 |
| Thymine | (+) | 8.0–11.0 |
| $\dfrac{A + G}{T + C}$ | | 0.87–1.01 |
| Molecular weight | | 10,000–100,000 |
| preferred molecular weight | | 15,000–60,000 |

(+) Those data relate to the corresponding percentage by weight on dry basis.

Coming now to the experiments by which the use by topical way of the above formulations has been contemplated, in order to reduce the couperose and the unaesthtisms of the skin areas of the lower limbs, it is worth to note that the primary common cause of said phenomena is to be evidently found in a modification of the normal conditions of the surface vessels, especially as regards their properties of mechanical strength.

In this connection it is firstly to be mentioned an experiment on animals (rats), in which the resistance of the capillary vessels had been reduced through the administration of a particular diet which, however, owing to repeated topical applications of formulations containing depolymerized deoxyribonucleic acids, showed at the end of the treatment period a relevant increase of the values of the capillary resistance in comparison with the starting conditions. The testing has been carried out on 55 animals, divided into six groups, as shown in Table II, and then treated by the formulations of Table III. Table IV illustrates the analytical properties of the deoxyribonucleic acids by which the compositions of the above-mentioned Table III have been prepared.

It is proper to note that in all cases the aforesaid formulations contained, as the active ingredient, an equal weight mixture of the batches of Table IV.

5 of the six afore-mentioned groups were fed with a vitamine P lacking diet (Charlier diet, as commercially available), which on the long run causes a relevant reduction of the mechanical strength of the capillary vessels (G. Rialdi: "Determinazione della resistenza capillare durante trattamento percutaneo con sostanze cheratoplastiche dotate di attivita anticouperosica" Riv. It. EPPOS 60 422–425 1978).

The capillary resistance was assessed from time to time according to Lavollay (J. Lavollay et al. "Problems posed by Activity of Certain Flavonoids on Vascular Resistance in Pharmacology of Plant Phenolics", Symposium Oxford, 1958, Proceedings Pag. 103–122 1959).

In order to carry out the required determination on the basis of the aforesaid technique, the skin of the lombar zone of the back was carefully shaved and slightly oiled with vaseline oil. The zone useful for the determination corresponded to an area of about 2×1.5 cm, extending by length from the last ribs and delimiting as to the width the paravertebral bands.

The animals were slightly anaesthetized and then, on the back area as previously individuated, the instrument for measuring the capillary resistance was applied, it essentially consisting of a sucker connected with a vacuum pump (petecchiometro, Baldinelli Milano).

The apparatus permits the value of the depression expressed as mm Hg, to be determined, which is capable of causing the capillary vessels to be broken.

Said determination has been effected in all groups of animals, fed with the Charlier diet, on the 21st day from the beginning of the experiment. It was found that in all groups the animals had the capillary resistance reduced in statistically significant manner with respect to the control group, the latter having been, on the contrary, fed with normal diet (MIL Morini diet).

Said reduction was furthermore statistically significant among the various groups. The capillary resistance in the treated animals was in absolute value of between 163.3 (group B) and 183.0 (group F); in the non treated animals (control group) it was of 319.6 mmHg.

The treatment by topical route was started on the 22nd day and prosecuted for seven consecutive days. The skin area of the animals, to which the formulations of Table III were applied, was the same on which previously the determination of the capillary resistance according to Lavollay had been carried out.

The administrations were repeated three times a day by topically applying 0.2 ml each time of each formulation of those above-referred to or 0.2 ml of physiological solution (control group).

At the end of the treatment period the capillary resistance was measured again according to the same technique. The results are reported in Table V.

As it can be seen, the topical application of the depolymerized deoxyribonucleic acids, as effected by means of the formulation of Table III and according to the experimental scheme which has been above-illustrated, has caused at all tested doses a statistically significant increase of the capillary resistance. From Table V it can moreover be seen that the preparation containing the depolymerized deoxyribonucleic acids at a 5% concentration (group E) has caused, in the rats which had been treated, an increase of the capillary resistance up to a value very close to that of the control group. It is worth to note also that the commercially available preparation containing as active ingredient the O-($\beta$-hydroxethyl)-rutosidea has been effective almost likely the gel containing the depolymerized deoxyribonucleic acids at a concentration of 1.25%.

TABLE II

Capillary fragility induced in the animal by administration of the Charlier diet. Groups, number of animals per group and related treatment.

| Group | No. of Animals | Treatment |
|---|---|---|
| A | 10 | Normal diet, topical treatment with physiological solution (control group). |
| B | 10 | Charlier diet, topical treatment with the "Placebo" formulation (Table III). |

TABLE II-continued

Capillary fragility induced in the animal by administration of the Charlier diet. Groups, number of animals per group and related treatment.

| Group | No. of Animals | Treatment |
|---|---|---|
| C | 10 | Charlier diet, topical treatment with 1.25% concentration gel (Table III). |
| D | 10 | Charlier diet, topical treatment with 2.50% concentration gel (Table III). |
| E | 10 | Charlier diet, topical treatment with 5% concentration gel (Table III). |
| F | 5 | Charlier diet, topical treatment with a commercially available preparation containing: O-($\beta$-hydroxyethyl)-rutosidea g 2, polymerized acrylic acid mg 600, disodium ethylendiaminotetracetate mg 50, benzalkonium chloride mg 5, bidistilled water balance to Kg 100 |

TABLE III

Composition of the cosmetic formulations used in the experiments of a capillary fragility.

| Components per 100 g of gel | | Placebo | 1.25% | 2.5% | 5% |
|---|---|---|---|---|---|
| Depolymerized deoxyribonucleic acids | g | — | 1.25 | 2.5 | 5 |
| Carbopol 940 | g | 2.0 | 2.0 | 2.0 | 2.0 |
| Propylene Glycol | g | 4.0 | 4.0 | 4.0 | 4.0 |
| Benzyl Alcohol | g | 1.4 | 1.4 | 1.4 | 1.4 |
| Isopropyl Alcohol | g | 2.0 | 2.0 | 2.0 | 2.0 |
| EDTA | g | 0.05 | 0.05 | 0.05 | 0.05 |
| Methyl p.Hydroxybenzoate | g | 0.15 | 0.15 | 0.15 | 0.15 |
| Propyl p.Hydroxybenzoate | g | 0.03 | 0.03 | 0.03 | 0.03 |
| 20% w/v NaOH | g | 4.0 | 4.0 | 4.0 | 4.0 |
| Distilled water balance to | g | 100 | 100 | 100 | 100 |

TABLE IV

Chemical and chemico-physical properties of the depolymerized deoxyribonucleic acids used in the formulations of Table III.

| Analytical Parameters | | Batch A | Batch B | Batch C |
|---|---|---|---|---|
| Phosphorus | (+) | 8.62 | 8.25 | 8.90 |
| Deoxyribose | (+) | 19.0 | 20.4 | 22.3 |
| Adenine | (+) | 10.0 | 10.1 | 9.6 |
| Guanine | (+) | 9.3 | 8.5 | 8.4 |
| Cytosine | (+) | 7.0 | 6.5 | 6.5 |
| Thymine | (+) | 10.5 | 9.7 | 9.4 |
| $\frac{A + G}{T + C}$ | | 0.93 | 0.97 | 0.95 |
| Molecular Weight | | 18,000 | 43,000 | 29,000 |

(+) The data are referred to the corresponding percentages by weight on dry basis.

TABLE V

Results relating to the effect of topical applications of preparations containing as active ingredients the deoxyribonucleic acids having the properties shown in Table I, on rats in which the fragility of surface capillary vessels had been experimentally induced by administration of the Charlier diet for 21 days before the beginning of the experiment. The applications have been continued for seven consecutive days, by determining the capillary resistance, according to the technique of Lavollay, before the beginning of the topical applications and at the end of the treatment period. The results reported hereinafter are expressed as mm Hg (average ± standard error).

| Group (ref. Table II) | Capillary Resistance before the Start (time 0) | Capillary Resistance at the End of Test | Difference vs. Time 0 | % Variation vs. Time 0 |
|---|---|---|---|---|
| A | 319.6 ± 6.7 | 320.6 ± 7.2 | 1.0 ± 5.0 | 0.3 |

TABLE V-continued

Results relating to the effect of topical applications of preparations containing as active ingredients the deoxyribonucleic acids having the properties shown in Table I, on rats in which the fragility of surface capillary vessels had been experimentally induced by administration of the Charlier diet for 21 days before the beginning of the experiment. The applications have been continued for seven consecutive days, by determining the capillary resistance, according to the technique of Lavollay, before the beginning of the topical applications and at the end of the treatment period. The results reported hereinafter are expressed as mm Hg (average ± standard error).

| Group (ref. Table II) | Capillary Resistance before the Start (time 0) | Capillary Resistance at the End of Test | Difference vs. Time 0 | % Variation vs. Time 0 |
|---|---|---|---|---|
| B | 163.3 ± 3.6 | 169.0 ± 5.5 | 5.7 ± 5.9 | 3 |
| C | 166.5 ± 6.5 | 175.0 ± 14.4 | 8.5 ± 14.0 | 5 |
| D | 169.8 ± 6.4 | 212.5 ± 11.0** | 42.7 ± 11.5** | 25 |
| E | 172.8 ± 5.2 | 237.5 ± 5.3** | 64.7 ± 5.9** | 37 |
| F | 183.0 ± 11.9 | 277.0 ± 10.7** | 94.0 ± 12.7** | 51 |
| G | 172.0 ± 5.0 | 209.0 ± 14.2** | 37.0 ± 9.7* | 22 |

*p 0.05
**p 0.01 "t" Student vs. Time 0

In order to confirm what was previously stated with respect to the common origin of the skin unaesthetisms which are here dealt with, as regards the couperose, is worth to observe that also from the literature (S. Curri et Alii "sostanze naturali ad azione sul microcircolo cutaneo" La Medicina Estetica Anno 4 n. 1 Gennaio/-Marzo 1980) there is demonstrated that the capillary fragility is an important factor in the genesis of this particular phenomenon.

The effectiveness of the depolymerized deoxyribonucleic acids in reducing the face couperose has been demonstrated by a test carried out on 10 patients of female sex, aged between 13 and 59 years (average age 34 years). The patients having flogistic lesions in the face or undergoing a treatment with drugs taken by systemic routes were excluded from the test. During the test the formulation of example 2 has been used. The active ingredient was a mixture of equal weights of the batches of depolimerized deoxyribonucleic acids of Table IV. The applications took place twice a day and were repeated for 60 consecutive days. The assessments were effected before the starting and at the end of the test, by transparency pictures, effected under standard lightening conditions and using a macro objective, the focus distance and opening of the diaphragm being constant. The pictures were taken in the morning, the patient being previously kept on resting for a period of 20 minutes in a room having controlled humidity and temperature.

The intensity of the colour of the skin, as assessed through the transparency pictures, has been thereafter processed by an apparatus for the measurement of the colour intensity (Chroma Meter Minolta chromometer), set for the measurement of the hemivector $a^*$ (chromometric coordinate set by the Lightening International Commission of 1976), corresponding to the green-red spectrum.

In this manner, it has been possible to quantitatively evaluate the red colour of the erythema.

Besides the aforesaid parameter instrument, also a subjective evaluation as regards the appearance of the reddening and the presence of dilated capillaries has been effected, on the basis of the following scores: 3=very evident, 2=averagely evident, 1=slightly evident.

In Table VI which follows are reported the obtained results. In order to better clarify the meaning of the reduction of the parameter $a^*$ which was detected at the end of the testing as a consequence of the treament with the formulation containing the aforesaid depolymerized deoxyribonucleic acids, it is to be mentioned that the same parameter, assessed in a population of 91 normal patients, was found as 13.00.

On the basis of Table VI it can be thus concluded that in this experiment the topical treatment with the aforesaid preparations has caused a significant improvement of the conditions of the patients' face.

TABLE VI

Reduction of the face couperose owing to the topical applications of formulations containing depolymerized deoxyribonucleic acids, as repeated twice a day for 60 days. The values which are reported relate to the parameter $a^*$ and to the subjective evalution of the reduction of the couperose through the corresponding score. The determinations (average ± standard error) have been effected before the starting of the treatment and after 60 days.

| Parameter | Time Zero | After 60 Days |
|---|---|---|
| $a^*$ | 19.17 ± 0.36 | 15.96 ± 0.45* |
| Subjective Evaluation (score) | 2.50 ± 0.17 | 1.70 ± 0.15* |

*P 0.01 Test "t" of Student

The effectiveness of the preparations containing depolymerized deoxyribonucleic acids, in order to reduce the skin phenomena at the lower limbs due to conditions of extended local fatigue, has been demonstrated by experiments carried out on 30 patients of female sex, aged between 30 and 50 years (average age of 40 years). All the patients showed oedemas at the ankles with very evident and dilated surface capillary vessels in the lower limbs. These phenomena were accompanied, in all cases under examination, by a feeling of pain and/or heaviness of the specific area of the leg.

The treatment period has been 60 days. The daily topical application has been effected on the whole leg. The formulation used in this experiment had the composition of example 4.

The active principle of the cream consisted of a mixture of equal weights of the three batches of Table IV. Before the beginning of the testing, after 30 and after 60 days, the following parameters have been evaluated:
subjective parameters: feeling of heaviness
objective parameters: ankle oedema, presence of possible areas of skin paleness.

The evaluation of the subjective and objective parameters has been effected by the method of the scores, by attributing a value, in arbitrary units, to the relevancy of the phenomenon on the basis of the following scale:

0=absent, 1=slight, 2=moderate, 3=strong, 4=very intense.

At the time zero and the end of the experiment also a capillaroscopic investigation has been effected at the ankle (lower third of the leg, medial area 5 cm above the internal malleolus), using a Wild-MS-C instrument connected with a photographic camera.

The study of the several pictures related to the diameter of the capillary vessels and the number of loops and the presence of possible microscopic haemorrhages. The magnitude of these assessments has been evaluated by the method of the scores by attributing a value, from 1 to 4, on the basis of the following scale:

1=worsened, 2=basic conditions, 3=improved, 4=highly improved.

The determination of the parameters as above-described has been effected in an afternoon period, so that the aforesaid skin phenomena appeared with the normal evidence.

The results are reported in the following Tables VII and VIII.

TABLE VII

Scores relating to the following clinical parameters: oedema, feeling of heaviness, areas of pale skin, measured at time zero and, respectively, after 30 and 60 days (average ± stadard deviation).

| Parameter | Time Zero | 30 Days | 60 Days |
|---|---|---|---|
| Oedema | 0.9 ± 0.2 | 0.4 ± 0.1* | 0.3 ± 0.1* |
| Feeling of Heaviness | 2.5 ± 0.1 | 1.3 ± 0.1* | 0.7 ± 0.2* |
| Pale Skin | 0.8 ± 0.2 | 0.5 ± 0.1* | 0.3 ± 0.1* |

*P 0.01

TABLE VIII

Modification of the average values of the scores relating to the global evaluation of the capillaroscopic examination at time zero and after 60 days (average ± standard deviation).

| Parameter | Time Zero | 60 Days |
|---|---|---|
| Capillaroscopic Analysis (scores) | 2.0 ± 0.0 | 3.1 ± 0.1* |

*P 0.01

From Tables VII and VIII it is evident that at the end of the experiment the improvement which had been obtained, owing to the repeated topical applications of the above formulation, was statistically significant for all the parameters under consideration.

It is worth to observe, with reference to the capillaroscopic examination that at the end of the period of the skin treatment the surface capillary vessels almost disappeared or were anyhow very attenuated.

The areas with oedema were totally absent.

EXAMPLE 1

Process for the Preparation of Depolymerized Deoxyribonucleic Acids from a High Molecular Weight DNA 1 kg of DNA extracted from small gut is dissolved in 200 liters of deionized water at 70° C. in which previously had also been dissolved 27 kg of trihydrated sodium acetate and 30 kg of glacial acetic acid.

The solution is then heated at 70° C. for four hours. It is at the end brought to neutral pH with 5N NaOH. The mixture is filtered leading to about 220 liters of solution. The depolimerized deoxyribonucleic acids are then precipitated by adding 24 liters of methanol (1.1 parts of solvent/part of solution). The precipitate is processed according to the standard technique, leading to about 650 g of product.

The analytical data relating to this preparation are the following ones (the data are expressed as percentage on dry basis): phosphorus 8.74, deoxyribose 18.3, adenine 9.4, guanine 7.8, cytosine 7.2, thymine 9.5, $$\frac{A + G}{T + C} = 0.88,$$

M.W. 58,000.

EXAMPLE 2

Anticouperose Cream

| Depolymerized Deoxyribonucleic Acids | g | 3 |
|---|---|---|
| Propyleneglycol | g | 5 |
| Tween 60 | g | 4.5 |
| Span 60 | g | 3 |
| Glyceril Monostearte | g | 8 |
| Isopropyl Miristate | g | 5 |
| Perfume and Preservants | | enough |
| Demineralized Water Balance to | g | 100 |

EXAMPLE 3

Anti-cellulitis Cream

| Depolymerized Deoxyribonucleic Acids | g | 3 |
|---|---|---|
| Polyethyleneglycol Stearate | g | 9 |
| Cetyl Alcohol | g | 5 |
| Propyleneglycol | g | 5 |
| Decyl Oleate | g | 10 |
| Perfume and Preservants | | enough |
| Demineralized Water Balance to | g | 100 |

EXAMPLE 4

Leg Cream

| Depolymerized Deoxyribonucleic Acids | g | 3.5 |
|---|---|---|
| Ethoxylated Fatty Alcohols | g | 7 |
| Acetoglyceril | g | 8 |
| 70% Sorbitan | g | 5 |
| Bee Wax | g | 4 |
| Perfume and Preservants | | enough |
| Demineralized Water Balance to | g | 100 |

EXAMPLE 5

Eye Contour Gel

| Depolymerized Deoxyribonucleic Acids | g | 4 |
|---|---|---|
| Carbopol 940 | g | 1.5 |
| Sodium Hydrate | g | 0.7 |
| Glycerine | g | 3 |
| Perfume and Preservants | | enough |
| Demineralized Water Balance to | g | 1 |

EXAMPLE 6

Lotion for Asphyctous Skins

| Depolymerized Deoxyribonucleic Acids | g | 1 |
|---|---|---|
| Glycerine | g | 5 |
| N.M.F. (Natural Moistening Factor) | g | 4 |
| Perfume and Preservants | | enough |

EXAMPLE 7

Pain Removing Cream

| Depolymerized Deoxyribonucleic Acids | g | 3 |
| --- | --- | --- |
| Self-emulsifying Base A/O | g | 20 |
| Almond Oil | g | 5 |
| Propyleneglycol | g | 5 |
| Perfume and Preservants | | enough |
| Demineralized water Balance to | g | 100 |

I claim:

1. A method for reducing a skin disorder selected from the group consisting of cellulitis, couperose, tumefactions, and local swelling, in a human in need of such treatment comprising topically applying an amount effective to reduce said skin disorder of at least one depolymerized deoxyribonucleic acid in a cosmetically acceptable carrier, said depolymerized deoxyribonucleic acid having a molecular weight of 10,000 to 100,000 Daltons.

2. The method of claim 1, wherein said depolymerized deoxyribonucleic acids contain, on a dry weight basis, 8.0–9.6% phosphorus, 13.0–15.0% nitrogen, 17.0–24.0% deoxyribose, 8.0–11.0% adenine, 7.0–9.5% guanine, 5.5–7.5% cytosine and 8.0–11.0% thymine.

3. The method of claim 1, wherein the molecular weight of said depolymerized deoxyribonucleic acid is from 15,000 to 60,000 Daltons.

4. The method of claim 1, wherein the amount of said depolymerized deoxyribonucleic acid is present in an amount of from 0.5 to 5.0% by weight of said composition.

5. The method of claim 1, wherein said depolymerized deoxyribonucleic acid is present in an amount of from 1 to 4% by weight of said composition.

* * * * *